United States Patent [19]

Smith

[11] Patent Number: 5,143,826
[45] Date of Patent: Sep. 1, 1992

[54] METHOD FOR IDENTIFYING FELINE BLOOD TYPE B

[75] Inventor: Joseph E. Smith, Manhattan, Kans.

[73] Assignee: Kansas State Univ. Research Foundation, Manhattan, Kans.

[21] Appl. No.: 611,185

[22] Filed: Nov. 9, 1990

[51] Int. Cl.$^5$ .................. G01N 33/53; G01N 33/48
[52] U.S. Cl. .................. 435/7.25; 436/520; 436/827; 424/11
[58] Field of Search ........... 435/7.25, 975; 436/8, 436/16, 827, 520; 424/11

[56] References Cited

PUBLICATIONS

Sigma Chemical Company Catalog, pp. 856–859, 881–882 and 1636 (1988).
AABB Technical Manual, Arlington VA: Amerian Association of Blood Banks, 1990:547–548.
Cain, Gary R. Et al., *Presumptive Neonatal Isoerythrolysis In Cats*, JAVMA, vol. 187, No. 1, Jul. 1, 1985, pp. 46–49.
Current Veterinary Therapy IX, Small Animal Practice, Pub. W. B. Saunders Co., 1986.
Giger, Urs, et al., *Frequencies of Feline Blood Groups in the United States*, JAVMA, vol. 195, No. 9, Nov. 1, 1989, pp. 1230–1232.
Hamanaka, Sumiko et al., *Occurrence of Hematoside with Two Moles of N-Acetyl-neuraminic Acid in a Certain Breed of Perian Cat*, J. Biochem. vol. 86, No. 3, 1979, pp. 695–698.
Hubler, M. et al., *Feline Neonatal Isoerythrolysis in Two Litters*, J. Small Anim. Pract. 28:833–838 (1987).
Nagata, Yoshiho et al., J. of Biol. Chem. vol. 249, No. 10, pp. 3116–3122 (1974).
Agre et al., "Molecular Biology of the Rh Antigens," Blood 78:551–563 (1991).
Furukawa et al., "Identification of N—Glycolylneuramic Acid–Containing Gangliosides of Cat an Sheep Erythrocytes, 252Cf Fission Fragment Ionization Mass Spectrometry in the Analysis of Glycosphinoglipids," J. Biol. Chem. 263:14939–14947 (1990).
Giger et al., "Frequency and Inheritance of A and B Blood Types in Feline Breeds of the United States," J. Hered. 82:15–20 (1991).
Rolih, "Biochemistry of MN Antigens," in Unger PJ, Laird–Fryer B (eds), Blood Group Systems, MN and Gerbich, Arlington, VA, American Association of Blood Banks, pp. 31–51 (1989).
Walker, "AABB Technical Manual,"(ed 10th), Arlington, VA American Association of Blood Banks, p. 529 (1990).

*Primary Examiner*—Esther L. Kepplinger
*Assistant Examiner*—Carol E. Bidwell
*Attorney, Agent, or Firm*—Tilton, Fallon, Lungmus & Chestnut

[57] ABSTRACT

The present invention relates to a method to detect feline blood type B comprising: combining feline blood with a sufficient amount of *Triticum vulgaris* lectin to agglutinate feline blood type B. Additionally, this invention relates to a kit to detect feline blood type B.

3 Claims, 1 Drawing Sheet

METHOD FOR IDENTIFYING FELINE BLOOD TYPE B

The Grant References research leading to this invention was supported in part by NIH Grant No. HLO1877-04 by the National Institute of Health. The U.S. Government has rights therein.

FIELD OF THE INVENTION

This invention relates to a method to identify feline blood type B using lectins.

BACKGROUND OF THE INVENTION

Various bloods have different antigenic and immune properties. These differences can be observed among different species and also between members of a species. Principally, these differences involve different antigens on the red blood cell wall and the immunological response to these antigens.

Human bloods have different antigenic and immune properties, and the four major groups are distinguished from each other by the presence or absence in the red blood cells of different, but related, antigens. Blood of group A contains antigen A, blood of group B contains only antigen B, blood of group O contains neither antigen A nor antigen B, and blood group AB contains only antigen AB.

Blood groups in cats, however, are different from blood groups in man. In cats two major feline blood groups were discovered in the 1950's with naturally occurring antibodies. The two feline erythrocyte antigens were designated A and B. Blood type B is rare in domestic cats, but is found in a much higher percentage in certain feline breeds. U. Giger et al., *Frequency of Feline Blood Groups in the United States*, J. Am. Vet. Med. Assoc. 1989; 195:1230–1232.

The presence in the cells of the antigens which are capable of immunological reaction with their respective antibodies, makes the cells susceptible to agglutination. When an antigen is not present in the red blood cell, the respective antibodies, called agglutinins, develop in blood plasma. Thus, for example, in man blood of group A contains anti-B antibodies in its serum and group O blood contains both anti-A and anti-B agglutinins. If bloods are mismatched, so that anti-A or anti-B antibodies are mixed with red blood cells containing A or B antigens, respectively, the red cells will agglutinate due to the immunological antigen/antibody reaction. This causes the cells to clump and thus block vessels, with usually fatal results.

Blood type B is a rare blood type in domestic cats, but is found in much higher percentage in certain feline breeds. U. Giger, et al. *Frequencies of Feline Blood Groups in the United States*, J. Am. Vet. Med. Assoc. 1989; 195:1230–1232. If a cat with blood type B is transfused with blood from a cat with blood type A, a serious life-threatening reaction may occur. In particular, if a female cat with blood type B is mated to a male cat with blood type A, the kittens may have neonatal isoerythrolysis and die. Neonatal isoerythrolysis is similar to Rh incompatibility in man. G. Cain et al., *Presumptive Neonatal Isoerythrolysis in Cats*, J. Am. Vet. Med. Assoc. 1985; 187:46–48; M. Huber et al., *Feline Neonatal Isoerythrolysis in Two Litters*, J. Small Anim. Pract. 1987; 28:833–838.

Agglutination reactions are widely used in biology and medicine to detect antibody or antigen molecules. Agglutination reactions usually involve the in vitro aggregation of microscopic carrier particles which bear on their surface antigenic molecules. An agglutination reaction can be caused by antibody molecules specifically corresponding to the antigen, an antigen, if the carrier particle is antibody coated or a protein that reacts with the surface antigenic molecules. The carrier particles include red blood cells, bacteria and polystyrene spheres. Blood typing makes use of this phenomena of agglutination to identify a cell type. In particular, feline blood type B is determined with antibodies produced in cats with blood type A. Cats of blood type A are immunized with B antigen. Antibodies against B antigen are produced by these cats. These antibodies are admixed with feline blood and theoretically agglutination should occur if B type antigens are present on the erythrocytes. In practice, however, these antibodies have been observed to be weak and unstable. See Giger, supra at 1231.

Consequently, a need exists to develop a reliable method to identify feline blood type B to decrease transfusion reactions and to be used to diagnose and prevent hemolytic disease in newborn cats.

SUMMARY OF THE INVENTION

The present invention relates to a method to identify feline blood type B comprising: adding a sufficient amount of a solution of lectin from *Triticum vulgaris* to feline blood. In particular, the feline blood may be whole blood or red blood cells. We have observed that erythrocytes agglutinate when the blood from the feline type B, but not type A, is mixed with a solution of lectin from *Triticum vulgaris*.

Additionally, this invention relates to a kit to detect feline blood type B.

DETAILED DESCRIPTION OF THE INVENTION

Figure 1:
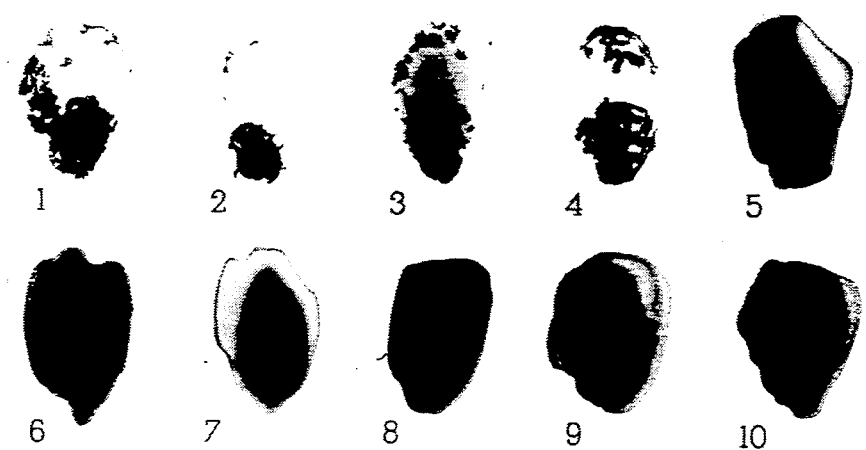
FIG. 1 shows the blood typing test of Example 2, conducted on an agglutination card.

The lectins from *Triticum vulgaris* will agglutinate blood type B feline erythrocytes, but not feline blood type A erythrocytes. This discovery allows cats with blood type B to be differentiated from those with blood type A.

Lectins are protein extracted from plant sources that react with specific complex sugars. Lectins have been used as group specific agglutinations for determining human blood groups. AABB Technical Manual, Arlington, Va: American Association of Blood Banks, 1990:547–548. Lectins from *Triticum vulgaris* have an affinity for N-acetyl-$\beta$-D-glucoaminyl residues, and N-acetyl-$\beta$-glucosamine oligomers. Y. Nagata et al., *Wheat Germ Agglutinin*, J. Biol. Chem. 1974, 249:3116–3123.

It was observed in the present invention that when *Triticum vulgaris* is incubated with feline red blood cells or whole blood, the erythrocytes agglutinated when the blood was from cats that were blood type B, but not blood type A. Additionally, it was observed that the feline antigen of blood group A may be NeuGC α 2-8NeuGc α 2-3Gal β 1-4Glc β 1-Ceramide and blood group B may be NeuAc α 2-8NeuAC α 2-3Gal β 1-4Glc β 1-Ceramide where NeuGC is N-glycolylneuraminic acid, NeuAc is N-acetylneuraminic acid, Gal is galactose, glc is glucose. We have also observed that this lectin will bind to glycoproteins.

Generally, the procedure of this invention involves combining a quantity of feline blood or washed feline erythrocytes, approximately four times the amount of feline blood, with a sufficient amount of a solution of *Triticum vulgaris* lectin, preferably, an amount four times greater than feline blood or an amount equal to washed feline erythrocytes. The preferred amount of lectin is 0.1 mg/mL of lectin per mL of buffer, but between about 0.2 to 0.05 mg/mL of lectin per mL of buffer can be used. If feline blood is used, to simplify the test one drop of feline blood can be combined with one drop of buffered *Triticum vulgaris* lectin. The *Triticum vulgaris* lectin is present in a phosphate buffered solution. The mixture is preferably incubated for 15 minutes at room temperature and then examined to detect agglutination. If an agglutination reaction occurs (i.e. 4+) the blood cells are typed B.

This method can be embodied in a kit by packaging a sufficient amount of *Triticum vulgaris* in a buffered solution. The kit may also include a microwell dilution plate or an agglutination card to conduct the test.

The following examples illustrate the patent invention and is not intended to limit the same.

EXAMPLE 1

Twenty-five microliters of feline blood (or 100 microliters of 2% washed feline erythrocytes) is combined with 100 microliters of a solution of *Triticum vulgaris* lectin (0.1 mg/mL of lectin per mL of phosphate buffered saline, pH 7.2) and incubated for 15 minutes at room temperatures. The reactions were read against a well-lit background and positive reactions were graded (Walker, 1990) from negative to 4+ where 4+ A single agglutinate. No free cells detected.

3+ Strong reaction. A number of large agglutinates.

2+ Large agglutinates in a sea of smaller clumps, no free cells.

1+ Many small agglutinates and a background of free cells.

Trace Appears negative macroscopically. A few agglutinates of 6-8 cells in most fields.

In Table 1 the results of agglutination tests on feline blood samples using *Triticum vulgaris* or anti-B antibodies are compared.

TABLE 1

| | Agglutination Reaction (Feline Whole Blood) | | | |
|---|---|---|---|---|
| Cat# | Triticum vulgaris lectin | Anti-blood type B Antibodies | Anti-blood type A Antibodies | Blood Type |
| 1 | 4+ | 3+ | Neg | B |
| 2 | 4+ | Unreadable | Neg | B |
| 3 | 4+ | 3+ | Neg | B |
| 4 | 4+ | 3+ | Neg | B |
| 5 | Neg | Neg | 2+ | A |
| 6 | Neg | Neg | 4+ | A |

TABLE 2

| | Agglutination Reaction (Feline Red Blood Cells - 2%) | | | |
|---|---|---|---|---|
| Cat# | Triticum vulgaris lectin | Anti-blood type B Antibodies | Anti-blood type A Antibodies | Blood Type |
| 1 | 4+ | 1+ | Neg | B |
| 2 | 4+ | 1+ | Neg | B |
| 3 | 4+ | 1+ | Neg | B |
| 4 | 4+ | 1+ | Neg | B |
| 5 | Neg | Neg | 4+ | A |
| 6 | Neg | Neg | 4+ | A |

EXAMPLE 2

One drop of feline blood is combined with one drop of *Triticum vulgaris* lectin (0.1 mg/mL of lectin per mL of phosphate buffered saline, pH 7.2) on an agglutination card. Within two minutes an agglutination reaction can be detected. In FIG. 1, spot nos. 1 to 4 show blood of cats with blood type B combined with *Triticum vulgaris* lectin. A strong agglutination can be observed. Spot nos. 5 and 10 show cats of blood type A. In spot no. 5, blood of a cat with blood type A is combined with *Triticum vulgaris* lectin. No agglutination was observed. In spots 6-9 blood of cats with blood type B is combined with anti B antibodies. Again, no agglutination is observed.

What has been described is a method to detect feline blood type B. Though the exemplary embodiment disclosed is preferred, numerous variations and modifications which do not part from the true scope of the invention will be apparent to those skilled in the art. All such variations and modifications are intended to be covered by the appended claims.

I claim:

1. A method to detect feline blood type B comprising:
   a. combining feline blood with a sufficient amount of buffered *Triticum vulgaris* lectin to agglutinate said feline blood type B;
   b. detecting agglutination; and
   c. correlating agglutination with feline blood type B.

2. The method of claim 1 wherein said blood is selected from the group consisting of feline whole blood and feline red blood cells.

3. The method of claim 1 wherein said lectin comprises a concentration about 0.1 mg/mL of lectin per mL of buffer.

* * * * *